United States Patent [19]

Bjellqvist et al.

[11] 3,956,371

[45] May 11, 1976

[54] METHOD FOR THE PREPARATION OF ALIPHATIC AND ALICYCLIC SULPHONIC ACIDS BY CATALYTIC SULPHOXIDATION OF HYDRO-CARBONS

[75] Inventors: Bengt G. Bjellqvist, Vasterhaninge; Torbjörn E. G. Westermark, Taby; Anders R. Axelsson, Stockholm; Martin J. Nilsson, Molndal, all of Sweden

[73] Assignee: Aminkemi AB, Bromma, Sweden

[22] Filed: Sept. 13, 1972

[21] Appl. No.: 288,832

Related U.S. Application Data

[63] Continuation-in-part of Ser. No. 885,975, Dec. 17, 1969, abandoned.

[30] Foreign Application Priority Data

Dec. 20, 1968 Sweden............................ 17533/68

[52] U.S. Cl............................ 260/503; 260/513 R
[51] Int. Cl.².................................... C07C 143/00
[58] Field of Search........... 260/513 R, 503, 504 R; 423/533, 538

[56] References Cited
UNITED STATES PATENTS

| | | | |
|---|---|---|---|
| 2,038,369 | 4/1936 | Lege | 260/504 R |
| 2,507,088 | 5/1950 | Bradley | 260/503 |
| 3,260,741 | 7/1966 | Mackinnon et al. | 260/513 R |
| 3,341,561 | 9/1967 | Starks | 260/513 R |
| 3,413,337 | 11/1968 | Bost | 260/513 R |

FOREIGN PATENTS OR APPLICATIONS

| | | | |
|---|---|---|---|
| 1,052,484 | 12/1966 | United Kingdom | 260/513 R |
| 414,913 | 6/1925 | Germany | 260/513 R |

OTHER PUBLICATIONS

Topchiev et al., Chem. Abstract, 51, 16111 e (1957).
E. E. Gilbert, "Sulfonation and Related Reactions," Interscience, N.Y. pp. 132–134 (1965).
Ambler et al. J. Industrial & Engineering Chem., 12, p. 968 (1920).

*Primary Examiner*—James O. Thomas, Jr.
*Assistant Examiner*—Nicky Chan
*Attorney, Agent, or Firm*—Fred Philpitt

[57] ABSTRACT

A process for the preparation of saturated, non-branched aliphatic or alicyclic sulphonic acids by reacting the corresponding hydrocarbons with sulphur dioxide and elementary oxygen is disclosed, in which process the reaction is carried out in the presence of copper as a catalyst. Reaction rates, considerably higher than those previously reported in literature, are obtained and the formation of by-products resulting in discolouration of the sulphonic acid is counteracted.

24 Claims, No Drawings

METHOD FOR THE PREPARATION OF ALIPHATIC AND ALICYCLIC SULPHONIC ACIDS BY CATALYTIC SULPHOXIDATION OF HYDRO-CARBONS

This application is a continuation-in-part of Ser. No. 885,975, filed Dec. 17, 1969, now abandoned.

The present invention relates to a method for the preparation of aliphatic and alicyclic sulphonic acids from the corresponding aliphatic and alicyclic hydrocarbons by catalytic sulphoxidation.

It is know, e.g. from the German patent specification No. 735,096, that sulphur dioxide and elementary oxygen can be caused to react with n-paraffins if the reaction is initiated with ultraviolet light, ozone or peroxides. During recent years the possibilities offered by this reaction for the preparation of tensides have created a renewed interest. This depends partly on the fact that the petroleum industry can now offer cheap hydrocarbons having the necessary chain length ($C_{10}$–$C_{18}$) and purity, and partly on the fact that the consumption of synthetic detergents which strongly increased in the fifties has increased the need for the tensides to be biologically decomposable. Alkane sulphonates are from this latter point of view superior to the linear alkylbenzene sulphonates.

According to the methods previously known the sulphoxidation is initiated by means of ultraviolet light, ozone, peroxides or, according to German patent specification No. 1,139,116, by means of gamma-radiation.

According to the present invention aliphatic or alicyclic sulphonic acids containing from 6 to 30 carbon atoms, inclusive, are prepared by catalytical sulphoxidation of the corresponding aliphatic or alicyclic hydrocarbons using copper either as the pure metal, alloyed or in the form of a chemical compound as a catalyst. Catalysts containing copper give rise to high reaction rates, which are considerably higher than those previously reported in literature, even when the comparison is made with experiments in which the energy was continuously supplied in the form of ultraviolet light or gamma radiation to carry out the sulphoxidation. For instance when using copper metal as the catalyst a reaction rate of about 130 g/l.h is obtained at a conversion of 5 – 9% by weight of a n-paraffin containing 13 – 17 carbon atoms, while the corresponding rate, when using gamma radiation, is reported to be about 20 g/l.h (Roesinger, International Atomic Energy Agency Symposium in Munich, August 18 – 22, 1969). Moreover, the metal catalyst has a controlling effect upon the reaction, whereby the formation of by-products resulting in discolouration of the sulphonic acid is conteracted.

An alternative previously known method to eliminate discolouration of the product due to formation of disulphonic acid and esters is the so-called light-water process described in German patent specification No. 910,165. This method, however, results in a strong formation of sulphuric acid whereby equivalent amounts of sulphonic acid and sulphuric acid are formed in the product. Moreover, the light-water process requires greater intensity of radiation in using gamma or ultraviolet radiation or alternatively a greater amount of catalyst in using ozone or peroxides in order to obtain the same reaction rate as in water-free systems.

A further possibility of influencing the sulphonation process by suspending a base, such as sodium hydroxide or sodium carbonate, in the hydrocarbon is described in literature (D. O. Hummel et al, Liebigs Ann. Chem. 673 (1964)page 13). The reaction is initiated by means of gamma radiation and the advantage obtained is an increased reaction rate. The reported rate of sulphonic acid formation is, however, lower than that obtained by using copper catalysts according to the present invention, and at the same time the relative amount of sulphuric acid in the reaction mixture increases, so that the product does not seem to be of improved quality.

In the British patent specification No. 1,052,484 there is described a catalytic process for the preparation of sulphonic acids from n-paraffins, sulphur dioxide and elementary oxygen. In this connection metals from the groups 5b – 7b and 8 of the periodic table in the form of salts of aliphatic carboxylic acids having 6 carbon atoms or more in the molecule are used. These catalysts are of an entirely different type. They require considerably longer periods of initiation than catalysts containing copper and the reaction rate will not be higher than would be obtained by initiation with gamma radiation or ultraviolet light without any addition of catalysts.

The gross reaction obtained on the direct sulphoxidation of hydrocarbons with sulphur dioxide and elementary oxygen can be written according to the following scheme:

$$RH + SO_2 + \tfrac{1}{2}O_2 \rightarrow RSO_3H$$

The reaction in reality proceeds as a linearly branched chain reaction in several stages with formation of, inter alia, persulphonic acid, $RSO_2O_2H$, as an intermediate.

The hydrocarbon used for the reaction should not contain very large amounts of impurities of aromatic, unsaturated or branched character, because otherwise the periods of initiation are too long. The hydrocarbon should be present in the form of a liquid in carrying out the reaction. In view of the usable range of temperature it is not possible to use n-paraffin mixtures, the main components of which contain more than about 30 carbon atoms. Copper is effective as a catalyst in the form of the pure metal, alloyed or bound in chemical compounds such as an oxide or a salt.

As examples of catalysts according to the invention may be mentioned copper metal e.g. in the form of a sheet or alloyed in the form of brass, furthermore copper-(I)-oxide and copper-(II)-oxide; copper salts of inorganic acids, e.g. copper-(I)-bromide, copper-(II)-bromide, copper-(I)-chloride, copper-(II)-chloride, copper-(I)-iodide, copper-(II)-nitrate, copper-(I)-chromite, copper-(I)-sulphite, copper-(II)-sulphate and copper-(II)-perchlorate; copper salts of organic acids, such as copper-(II)-formate, the salts of aliphatic monocarboxylic acids having 2 to 18 carbon atoms, e.g. copper-(II)-acetate, copper-(II)-propionate, copper-(II)-butyrate, copper-(II)-laurate, copper-(II)-palmitate, copper-(II)-stearate; copper-(II)-methane sulphonate, copper-(II)-cyclohexane sulphonate and copper-(II)-chloroacetate. These catalysts are effective even in very small amounts (magnitude 1 mg/l) with respect to guiding the reaction and increasing the reaction rate. However, also copper salts of acids containing groupings known to act as strong inhibitors of the sulphoxidation process are surprisingly found to be active as catalysts for said process, which effect should be assigned to the presence of the copper. Examples of copper salts of this type are copper-(II)-benzoate, copper-(II)- butenoate, copper-(II)-oleate and copper-(II)-phenyl acetate.

If copper in the form of a chemical compound is used it is dissolved in the hydrocarbon if possible. If the catalyst is not soluble to a sufficient extent it is dispersed in finely divided form in the hydrocarbon. Amounts of catalyst corresponding to between 300 mg/l and 10 g/l at room temperature will cause the reaction to proceed at a considerable rate within periods of about 1 hour or less. The main part of the copper supplied in the form of a chemical compound will be present in the form of the hydrogen sulphate and the sulphonate in the reaction mixture. In many cases it may be desirable to reduce the amount of catalyst in order to obtain a lower content of copper in the product. The extension of the initiation period obtained at the same time can be counteracted by increasing the temperature in the initial stage of the reaction or by using ultraviolet light, ionizing radiation, ozone or peroxide to shorten the initiation time. Alternatively, the sulphoxidation can be initiated by transferring a minor amount of the reacting hydrocarbon to a reaction vessel containing a large quantity of reaction mixture, without it being necessary to supply any additional catalyst. When the sulphoxidation is carried out continuously, no subsequent addition of catalyst will be necessary to carry out the sulphoxidation process after the reaction has once been initiated. When a high reaction rate is desired, a minor amount of catalyst may be supplied continuously together with the hydrocarbon.

If copper metal is used as a catalyst and is immersed in the form of a sheet or a net into the reaction mixture, it will be dissolved in amounts corresponding to between 0.005 and 5 mg of copper per g of sulphonic acid formed.

The sulphoxidation of the hydrocarbon in the presence of a catalyst may be carried out at a temperature in the range of from 0°C to +60°C, most suitably in the range of from +10°C to 40°C. Higher temperatures will result in increased formation of by-products and discolouration of the product. The reaction being exothermic, it will be necessary to cool the reaction mixture in order to avoid undesirable temperature rises. During the step of initiation it may, however, be advantageous to work at an increased temperature because the initiation period can thereby be shortened. Preferably the reaction is carried out at atmospheric pressures or above as the reaction rate increases according to the pressure. Sulphur dioxide and elementary oxygen may be supplied in molar ratios varying between 1:1 and 40:1, molar ratios exceeding the stoichiometric ratio 2:1 being preferred. If desired, air may be used instead of oxygen gas.

The further the reaction of the hydrocarbon is carried out the higher will be the content of polysubstituted sulphonic acids in the product. Polysubstituted sulphonic acids are not surface-active and when present in large amounts they may reduce the surface activity of the monosulphonate. In view of this, a conversion of 0.5 to 10% by weight preferably 1 to 5% by weight of the hydrocarbon is chosen for the preparation of sulphonic acids for later use as washing detergents.

The reaction time required depends upon the particular catalyst used, the amount of catalyst, the quality of the hydrocarbon, the ratio of $SO_2$ to $O_2$, the temperature and the pressure, and may vary from a few minutes to several days. In our experiments reaction times in the range of from 1 to 24 hours have been used.

The sulphoxidation may be carried out continuously as well as discontinuously. Most conveniently the sulphoxidation process is carried out discontinuously and under such pressure and temperature conditions that the sulphur dioxide is in the form of a gas. The gaseous ingredients, sulphur dioxide and elementary oxygen, can be passed through the hydrocarbon in which the catalyst has been dispersed or dissolved. It is not necessary to use pressure vessels and the necessary agitation can be attained by suitably selecting the gas flow rate.

The sulphonic acid formed can be separated out from the reaction mixture by adding 2 – 5% by weight of water.

EXAMPLE 1

Sulphoxidation of cyclohexane using copper-(I)-oxide as catalyst

In a glass reaction vessel of capacity 100 ml, 0.3 g of finely divided copper-(I)-oxide was dispersed in 50 ml of cyclohexane. Sulphur dioxide and oxygen gas were passed into the vessel through a glass filter situated beneath the surface of the liquid using a flow rate of 10 l/h and 5 l/h, respectively, for the sulphur dioxide and the oxygen gas. The experiment was carried out at atmospheric pressure and the temperature was constantly held at 25°C throughout the experiment, which lasted for 6 hours. The product was extracted from the hydrocarbon phase by means of water. Analysis, carried out as a pH-titration in a mixture of acetone and water, showed that the product contained 148 m. moles of sulphonic acid and 26 m. moles of sulphuric acid.

EXAMPLE 2

Sulphoxidation of cyclohexane using copper-(I)-oxide as catalyst

In this experiment 0.015 g of copper-(I)-oxide was dispersed in 50 ml of cyclohexane in the reaction vessel. The flow rates of the gases and the reaction conditions were the same as those used in Example 1. Analysis showed that the product obtained after reaction for 6 hours contained 108 m. moles of sulphonic acid and 15 m. moles of sulphuric acid.

EXAMPLE 3

Sulphoxidation of n-hexane using copper-(I)-oxide as catalyst

Example 1 was repeated using n-hexane instead of cyclohexane. After reaction for 6 hours, a product comprising 135 m. moles of sulphonic acid and 28 m. moles of sulphuric acid was obtained.

EXAMPLE 4

Sulphoxidation of cyclohexane using copper-(I)-oxide as catalyst and air instead of oxygen gas Example 1 was repeated using 0.15 g of copper-(I)-oxide and instead of oxygen gas a stream of air at a flow rate of about 23 l/h was used. The reaction was carried out for 8 hours yielding 66 m. moles of sulphonic acid.

EXAMPLE 5

Sulphoxidation of cyclohexane using copper metal as catalyst

Example 1 was repeated but instead of copper-(I)-oxide, copper was added to the reaction vessel in the form of a sheet weighing 2.98 g and having an area of 91.2 cm². The reaction was carried out for 9.5 hours. Weighing of the copper sheet after the experiment showed a loss in weight of 30 mg. Analysis showed that the product contained 166 m. moles of sulphonic acid and 24.3 m. moles of sulphuric acid.

EXAMPLE 6

Sulphoxidation of n-parraffin ($C_{12}$-$C_{16}$) using brass as catalyst and gamma-radiation for initiation of the reaction The copper sheet in Example 5 was replaced by a sheet of brass. 50 ml of n-paraffin ($C_{12}$-$C_{16}$) were introduced into the reaction vessel. The reaction was carried out for half an hour during which time the reaction vessel was immersed in a $Co^{60}$ gamma-source, which with the exploited geometry gave a dose rate of 0.72 Mrad/h. As to the other reaction conditions those of Example 1 were used. Analysis showed that the product contained 10.3 m. moles of sulphonic acid. When a corresponding experiment was carried out with no brass present 4.4 m. moles of sulphonic acid were obtained.

EXAMPLE 7

Sulphoxidation of n-paraffin ($C_{11}$-$C_{12}$) using copper metal as catalyst and excess sulphur dioxide The copper was present in the form of a sheet weighing 4.63 g and having an area of 75 cm². 50 ml of n-paraffin ($C_{11}$-$C_{12}$) were introduced into the reaction vessel. The flow rates of sulphur dioxide and oxygen gas were 27 l/h and 3 l/h, respectively. The reaction was carried out for 3 hours at 25°C. Weighing of the copper sheet showed a loss in weight of 5.8 mg. The product contained 57.2 m. moles of sulphonic acid and 17.7 m. moles of sulphuric acid.

EXAMPLE 8

Sulphoxidation of n-paraffin ($C_{11}$-$C_{12}$) using copper metal as catalyst and excess of sulphur dioxide In this experiment the area of the copper sheet was 75 cm². 50 ml of n-paraffin ($C_{11}$-$C_{12}$) were introduced into the reaction vessel. The total flow rate of the gas was 30 l/h and the gas employed consisted of 97.5% of sulphur dioxide and 2.5% of oxygen gas. The reaction time was 8 hours. The product contained 60 m. moles of sulphonic acid and 14 m. moles of sulphuric acid. The loss in weight of the copper sheet was 51.5 mg.

EXAMPLE 9

Sulphoxidation of n-paraffin ($C_{22}$-$C_{28}$) using copper metal as catalyst and excess sulphur dioxide The copper sheet was identical with the one used in Example 7 and the flow rates of the gas streams were 27 l/h and 3 l/h of sulphur dioxide and oxygen gas respectively. The paraffin employed, 40 g of which were used in the experiment, was liquefied at 51°C and the reaction was carried out at 60°C for 24 hours. Analysis showed that 6 m. moles of sulphonic acid were formed.

EXAMPLE 10

Sulphoxidation of cyclohexane using copper-(I)-chloride as catalyst 0.10 g of copper-(I)-chloride was dispersed into 50 ml of cyclohexane. The flow rates of sulphur dioxide and oxygen gas were 10 l/h and 5 l/h, respectively. No external cooling was applied and because of this the temperature in the reaction vessel increased to between 50°C and 60°C during the most intense phase of the reaction. After 10 hours the experiment was interrupted. The product then contained 220 m. moles of sulphonic acid and 56 m. moles of sulphuric acid.

EXAMPLE 11

Sulphoxidation of cyclohexane using copper-(II)-acetate as catalyst

Example 10 was repeated but in this experiment 0.2 g of $Cu(CH_3COO)_2.H_2O$ was used as a catalyst and the reaction was interrupted after 3 hours and 40 minutes. In the product phase 97 m. moles of sulphonic acid and 18 m. moles of sulphuric acid could be established.

EXAMPLE 12

Sulphoxidation of n-paraffin ($C_{11}$-$C_{12}$) using copper-(II)-acetate as catalyst Example 7 was repeated but as catalyst 0.7 g of $Cu(CH_3COO)_2.H_2O$ was used. During a reaction time of 8 hours 97 m. moles of sulphonic acid and 19 m. moles of sulphuric acid were formed.

EXAMPLE 13

Sulphoxidation of n-paraffin ($C_{11}$-$C_{12}$) using copper stearate as catalyst Example 7 was repeated but 0.05 g of copper stearate was used as catalyst. During a reaction time of 8 hours 43 m. moles of sulphonic acid and 13 m. moles of sulphuric acid were formed.

EXAMPLE 14

Continuous sulphoxidation of n-paraffin ($C_{10}$-$C_{13}$) using copper metal as a catalyst 100 ml of n-paraffin ($C_{10}$-$C_{13}$) were placed in a reaction vessel provided with an agitator and a cooling coil. A sheet of copper metal was placed within the body of the hydrocarbon liquid, said sheet presenting a total area of 50 cm². A gaseous mixture consisting of 90 percent of sulphur dioxide and 10 percent of elementary oxygen was introduced into the hydrocarbon at a rate of 30 liters per hour via a filter arranged near the bottom of the reaction vessel. The temperature of the reaction mixture was maintained constant at 25°C by cooling. The gas flow rate was measured before the gas entered and after the gas left the reaction vessel. After supplying the gas for 80 minutes a difference in volume between the supplied and discharged gases amounting to 62 millilitres per minute could be observed, said difference corresponding to a formation rate of 0.08 mole of sulphonic acid per hour. Treated hydrocarbon was then continuously discharged through an outlet in the bottom of the reaction vessel. The discharge flow rate was held at 5.5 milliliters per minute. The reaction volume was maintained constant by supplying fresh paraffin to the reaction vessel. A minor decrease in reaction rate was obtained after the continuous operation of the reaction vessel had begun. 1 percent by volume of water was added to the discharged reaction mixture and the new mixture thus obtained was subjected to phase separation, one aqueous phase and one hydrocarbon phase being obtained. The aqueous phase contained 34 percent of sulphonic acid. This corresponds to a rate of sulphonic acid formation amounting to 0.35 gram per minute, that is 210 grams per litre and hour. After the phase separation, the hydrocarbon phase could be returned directly to the reaction vessel without adversely affecting the rate of the sulphonic acid formation.

EXAMPLE 15

Sulphoxidation of n-paraffin ($C_{13}$-$C_{17}$) using copper metal as catalyst and excess sulphur dioxide In this experiment, the copper was present in the form of a sheet weighing 3.876 g and having an area of 75 cm$^2$. The gas flow rates of sulphur dioxide and oxygen were 2.4 and 0.27 l/h, respectively. 50 ml of n-paraffin ($C_{13}$-$C_{17}$) were introduced into the reaction vessel. The experiment was carried out at 25°C for 2 hours. Weighing of the sheet showed a loss in weight of 2.6 mg. The product contained 20.7 m. moles of sulphonic acid and 7.3 m. moles of sulphuric acid according to analysis.

EXAMPLE 16

Sulphoxidation of n-paraffin ($C_{10}$-$C_{13}$) using copper metal as catalyst and excess sulphur dioxide The copper sheet was identical with the one used in Example 15. 50 ml of n-paraffin ($C_{10}$-$C_{13}$) were introduced into the reaction vessel. The gas flow rates of sulphur dioxide and oxygen were 13.5 l/h and 1.5 l/h, respectively. The experiment was carried out at 25°C and lasted for 90 minutes. The loss in weight of the copper plate was 1.2 mg. The product contained 2.8 m. moles of sulphonic acid and 1.8 m. moles of sulphuric acid according to analysis.

EXAMPLE 17

Sulphoxidation of n-paraffin ($C_{10}$-$C_{13}$) using copper metal as catalyst and excess sulphur dioxide The conditions were identical with those used in Example 16 but the experiment lasted for 1 h 50 min. The loss in weight of the copper sheet was 2.3 mg and the product contained 7.7 m. moles of sulphonic acid and 4.4 m. moles of sulphuric acid according to analysis.

EXAMPLE 18

Sulphoxidation of cyclohexane using copper-(I)-sulphite as catalyst

Example 10 was repeated but in this experiment 0.2 g $Cu_2SO_3$ was used as catalyst. During a reaction time of 6 hours 235 m. moles of sulphonic acid and 78 m. moles of sulphuric acid were formed.

EXAMPLE 19

Sulphoxidation of cyclohexane using copper-(II)-nitrate as catalyst

Example 10 was repeated but in this experiment 0.2 g $Cu(NO_3)_2 \cdot 3H_2O$ was used as catalyst. During a reaction time of 6 hours 120 m. moles of sulphonic acid 35 m. moles of sulphuric acid were formed.

EXAMPLE 20

Sulphoxidation of cyclohexane using copper-(I)-chromite

Example 10 was repeated but in this experiment 0.2 g $Cu_2Cr_2O_4$ was used as catalyst. During a reaction time of 6 hours 180 m. moles of sulphonic acid and 48 m. moles of sulphuric acid were formed.

What we claim is:

1. In the known process for the preparation of saturated, non-branched alkyl or cycloalkyl sulphonic acids containing from 6 to 30 carbon atoms inclusive by reacting the corresponding alkane or cycloalkane with sulphur dioxide and elementary oxygen in the presence of a catalyst, the improvement which comprises using copper as the catalyst, the copper being added in the form of copper metal, an oxide or a salt, the salt being the salt of an inorganic or an organic acid and either dissolved or dispersed in the alkane or cycloalkane.

2. A process as claimed in claim 1 in which the reaction is carried out at temperatures between 0°C and +60°C.

3. A process as claimed in claim 1 in which the reaction is carried out at a temperature between +10°C and +40°C.

4. A process as claimed in claim 1 in which sulphur dioxide and elementary oxygen are supplied in a molar ratio between 1:1 and 40:1.

5. A process as claimed in claim 1 in which sulphur dioxide and elementary oxygen are supplied in a molar ratio exceeding 2:1 and at most amounting to 40:1.

6. A process as claimed in claim 1 in which elementary oxygen is supplied in the form of air.

7. A process as claimed in claim 1 in which water is supplied to the reaction mixture to extract the product.

8. The process of claim 1 wherein the cycloalkane is cyclohexane.

9. The process of claim 1 wherein the alkane is n-hexane.

10. The process of claim 1 wherein the alkane is n-paraffins.

11. The process of claim 1 wherein copper is added in the form of an oxide or a salt whereby copper is present in the form of the hydrogen sulfate and the sulphonate in the reaction mixture.

12. The process of claim 1 wherein copper is added in the form of a salt of an inorganic acid.

13. The process of claim 1 wherein copper is added in the form of a salt of an alkanoic acid having from 2 to 18 carbon atoms.

14. The process of claim 11 wherein copper is present in the form of the salt of the sulphonic acid formed from the alkane or cycloalkane used as starting material.

15. In the known process for the preparation of saturated, non-branched alkyl or cycloalkyl sulphonic acids containing from 6 to 30 carbon atoms inclusive by reacting the corresponding alkane or cycloalkane with sulphur dioxide and elementary oxygen in the presence of a catalyst, ozone or peroxide being supplied to the reaction mixture at the initiation of the reaction, the improvement which comprises using copper as the catalyst, the copper being added in the form of copper metal, an oxide or a salt, the salt being the salt of an inorganic or an organic acid and either dissolved or dispersed in the alkane or cycloalkane.

16. A process as claimed in claim 15 in which the reaction is carried out at temperatures between 0°C and +60°C.

17. A process as claimed in claim 15 in which sulphur dioxide and elementary oxygen are supplied in a molar ratio between 1:1 and 40:1.

18. In the known process for the preparation of saturated, non-branched alkyl or cycloalkyl sulphonic acids containing from 6 to 30 carbon atoms inclusive by reacting the corresponding alkane or cycloalkane with sulphur dioxide and elementary oxygen in the presence of a catalyst, the alkane or cycloalkane being converted to the alkyl or cycloalkyl sulphonic acid to a degree of 0.5 to 10% by weight, the improvement which comprises using copper as the catalyst, the copper being added in the form of copper metal, an oxide or a salt, the salt being the salt of an inorganic or an organic acid and either dissolved or dispersed in the alkane or cycloalkane.

19. A process as claimed in claim 18 in which the degree of conversion is 1 to 5% by weight.

20. A process as claimed in claim 18 in which the reaction is carried out at temperatures between 0°C and +60°C.

21. A process as claimed in claim 18 in which sulphur dioxide and elementary oxygen are supplied in a molar ratio between 1:1 and 40:1.

22. A process as claimed in claim 18 in which at the initiation of the reaction ozone or peroxide is supplied to the reaction mixture.

23. In the known process for the preparation of saturated non-branched alkyl or cycloalkyl suphonic acids containing from 6 to 30 carbon atoms inclusive by reacting the corresponding alkane or cycloalkane with sulphur dioxide and elementary oxygen in the presence of a catalyst, the improvement which comprises using copper as the catalyst, the copper being added in the form of a member selected from the group of pure copper metal, brass, $Cu_2O$, $Cu_2SO_3$, $CuCl$, $CuO$, $Cu(CH_3COO)_2$, and cupric stearate.

24. The process of claim 23 wherein at the initiation of the reaction ozone or peroxide is supplied to the reaction mixture.

* * * * *